(12) United States Patent
Lynn

(10) Patent No.: US 6,545,951 B1
(45) Date of Patent: *Apr. 8, 2003

(54) DIGITAL MENSTRUAL WRISTWATCH

(76) Inventor: Lynn Lynn, 19 W. 10th St., Apartment No. 8, New York City, NY (US) 10011

( * ) Notice: Subject to any disclaimer, the term of this patent is extended or adjusted under 35 U.S.C. 154(b) by 0 days.

This patent is subject to a terminal disclaimer.

(21) Appl. No.: 08/803,624

(22) Filed: Feb. 21, 1997

Related U.S. Application Data

(63) Continuation of application No. 08/564,625, filed on Nov. 29, 1995, now Pat. No. 5,606,535.

(51) Int. Cl.⁷ .............................. G04B 19/00; A61B 5/00
(52) U.S. Cl. ........................ 368/223; 368/10; 368/107; 600/551
(58) Field of Search .......................... 368/10, 107–113; 600/551

(56) References Cited

U.S. PATENT DOCUMENTS

| | | | |
|---|---|---|---|
| 3,964,674 A | * 6/1976 | VanGaast | 368/37 |
| 4,101,962 A | * 7/1978 | Hakata | 708/161 |
| 4,151,831 A | * 5/1979 | Lester | 368/10 |
| 4,367,527 A | * 1/1983 | Desjacques | 368/10 |
| 4,443,851 A | * 4/1984 | Lin | 600/551 |
| 4,488,560 A | * 12/1984 | Takamura | 600/551 |
| 4,527,906 A | * 7/1985 | Jezbera | 368/107 |
| 5,043,888 A | * 8/1991 | Uriarte | 364/413.12 |
| 5,058,085 A | * 10/1991 | Lawler | 368/28 |
| 5,515,344 A | * 5/1996 | Ng | 368/10 |
| 5,606,535 A | * 2/1997 | Lynn | 368/10 |
| 5,777,905 A | * 7/1998 | Dowdle et al. | 600/551 |

* cited by examiner

Primary Examiner—Vit Miska
Assistant Examiner—Jeanne-Marguerite Goodwin
(74) Attorney, Agent, or Firm—De La Rosa & De La Rosa, LLC

(57) ABSTRACT

The present invention is an electronic device or chronometer for use by women of various ages to monitor their menstrual, ovulation and menopausal cycles. The chronometer displays information relating to a woman's menstrual cycle readily useful to the woman, including the dates of her last and next menstrual cycles, the number of days that have elapsed since the last menstrual cycle, and the next ovulation day. If desired, the day(s) a woman expects PMS can also be displayed, such as for those who severely experience the associated symptoms.

20 Claims, 6 Drawing Sheets

DIGITAL MENSTRUAL WRISTWATCH

CROSS-REFERENCE TO RELATED APPLICATION

This is a continuation of U.S. patent application Ser. No. 08/564,625, entitled "Digital Menstrual Wristwatch" filed on Nov. 29, 1995 U.S. Pat. No. 5,606,535, which is incorporated herein by reference.

TECHNICAL FIELD

The present invention relates generally to menstrual cycle indicators, and more particularly, to digital wristwatches for monitoring women's menstrual, ovulation, and menopausal cycles.

BACKGROUND OF THE INVENTION

It is well known in the art that a woman's menstrual cycle occurs approximately once a month. For obvious reasons, women monitor the number of days that have passed since their last menstrual cycle or so-called "menses." Indeed, most women, if not all, mark off a fixed number of days from their last menstrual cycle on a calendar to determine when their next period is due. While this method is simple and inexpensive, it also has a number of drawbacks. First, a woman must remember the date of her last menstrual cycle. Second, if a woman incorrectly counts the number of days from her last cycle, she will also make a mistake when her next menstrual cycle or period is due. Third, women who monitor their ovulation, such as for birth control or fertility, can likewise incorrectly count the number of days, and thereby erroneously time the period during which to abstain from or engage in sexual intercourse. Similarly, using this latter method, women can also make a mistake about when to expect pre-menstrual syndrome (PMS), which occurs several days before and after a woman's period.

In the prior art, various attempts have been made for monitoring a woman's menstrual cycle. Most notably, U.S. Pat. No. 4,527,906 to Jezbera discloses a digital watch module that displays the number of days that have passed since the start of a woman's last menstrual cycle. One primary drawback of the foregoing prior art, however, is its inability, among other things, to display information relating to a woman's menstrual cycle in a manner that is readily useful to a woman. For example, from the displayed information of Jezbera, a woman must still use, for example, a calendar to determine the dates of her last and next menstrual cycles, as well as the dates of her ovulation and pre-menstrual syndrome.

Another drawback in the prior art is its inability to automatically monitor for variations in a woman's cycle. This is especially important inasmuch as women's cycles vary by an average of about seven to thirteen days for peak reproductive years and by even a greater amount for girls in their teens and women approaching menopause.

SUMMARY OF THE INVENTION

An object of the present invention, therefore, is to provide an electronic device or chronometer for use by women of various ages to monitor their menstrual, ovulation and menopausal cycles. More specifically, an object of the present invention is to display information relating to a woman's menstrual cycle that is readily useful to the woman, including the dates of the last and next menstrual cycles, the number of days that have elapsed since the last menstrual cycle, and date of the next ovulation. If desired, the day(s) a woman expects PMS can also be displayed, such as for those who severely experience the associated symptoms.

A further object of the invention is to automatically monitor for variations in the woman's menstrual cycle, compared to, for example, the actual number of days in her menstrual cycles from previous months.

A further object of the present invention is to provide such a display in conjunction with the current time, day, month and year as well as in conjunction with the display of a standard calendar.

A further object of the present invention is to provide alarms to the woman, programmable one to several days before the start of the menstrual cycle, so as to alert the woman that she is within a target range, either relating to ovulation or pre-menstrual syndrome.

These and other objects of the present invention are achieved by arranging display windows on the face of a digital wristwatch which windows are programmable to display the date of the last menstrual cycle, the date of the next menstrual cycle, the number of days since the last menstrual cycle and the date of ovulation.

In a preferred embodiment, the present invention is a microprocessor-based watch responsive to inputs from a user, including the date of her last menstrual cycle and the number of days in the woman's menstrual cycle. In response to such inputs, the microprocessor automatically calculates or estimates the woman's ovulation day and the date of her next menstrual cycle for the purpose of displaying such information to the woman.

Also, the preferred embodiment of the invention includes a look-up table or memory which stores information about a woman's previous menstrual cycles which may be used in determining the date of the woman's next menstrual cycle or ovulation day. Also, such prior menstrual history may be used to account or monitor for variations in a woman's menstrual cycle. Furthermore, such information may be retrieved and used for medical diagnostics, if the woman later becomes ill.

In the preferred embodiment, an annular portion of the display may be segmented into equally spaced divisions and used to visually indicate the number of days that have passed since the last menstrual cycle began.

BRIEF DESCRIPTION OF THE DRAWING

Other objects, features and advantages of the invention will become apparent from the following description, together with the accompanying drawings in which like elements are labeled similarly and in which.

DETAILED DESCRIPTION

Without any loss of generality or applicability for the principles of the present invention, the embodiments below herein are directed to a digital wristwatch. It should be understood, however, that the present invention is equally applicable to other types of chronometers, such as clocks or personal computers that function as chronometers.

Figure 1:
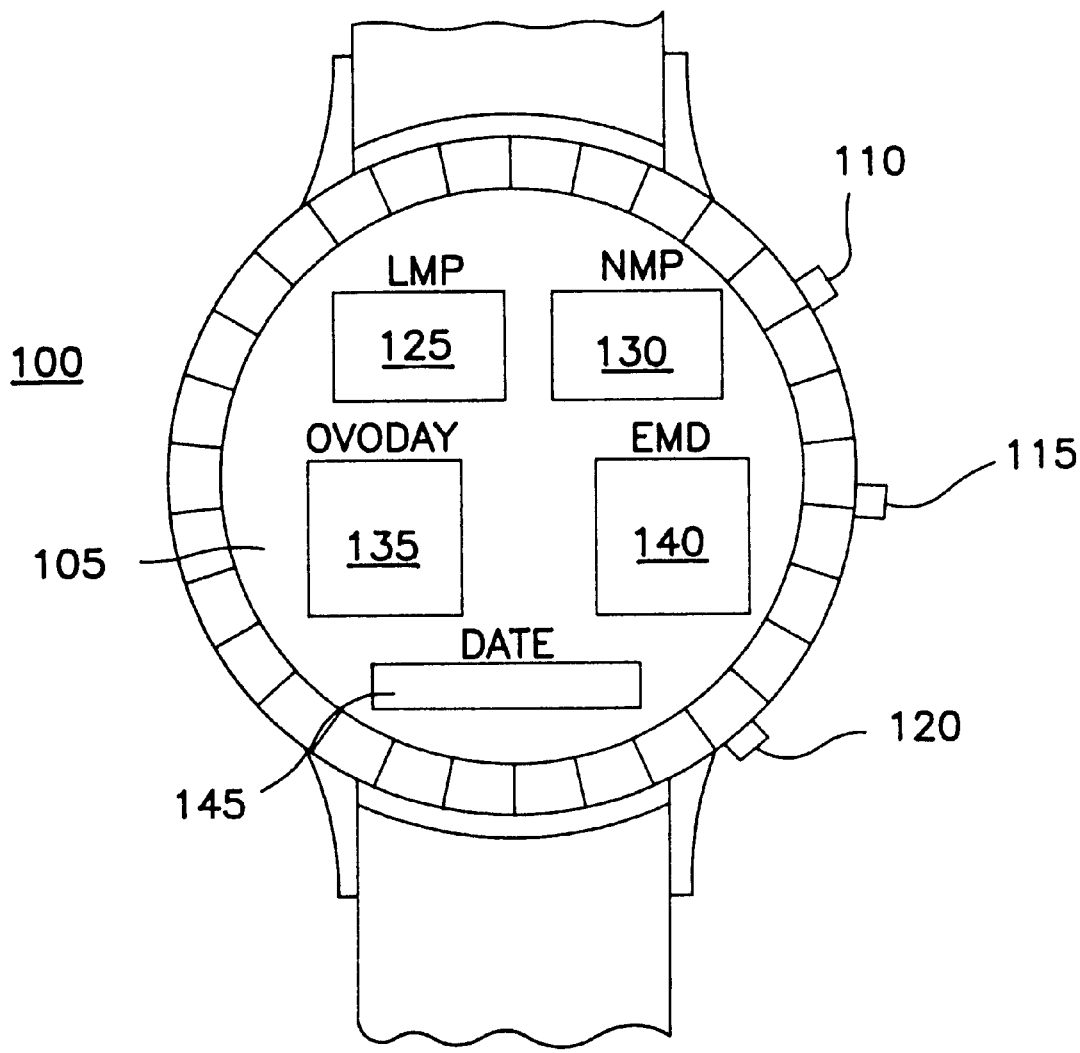
FIG. 1 is a plan view of a digital menstrual wristwatch in accordance with the principles of the invention.

The overall operation of the digital menstrual watch of the present invention may be most easily understood by first referring to FIGS. 1–4. Referring to FIG. 1 there is shown a digital menstrual wristwatch 100 having a LCD face 105, pushbuttons 110, 115, 120, and display windows 125, 130, 135, 140 and 145. Display windows 125, 130, 135, 140 and 145 display the date of a woman's last menstrual period ("LMP"), the date of a woman's next menstrual period ("NMP"), the expected ovulation day ("ovoday") and the number of days that have elapsed since the beginning of the last menstrual period ("EMD"), and the current time and day, respectively. The display windows may be reset to display corresponding information about last month's menstrual cycle when pushbutton 110 is depressed once, and about the month prior to that when depressed twice, and so on.

Figure 2:
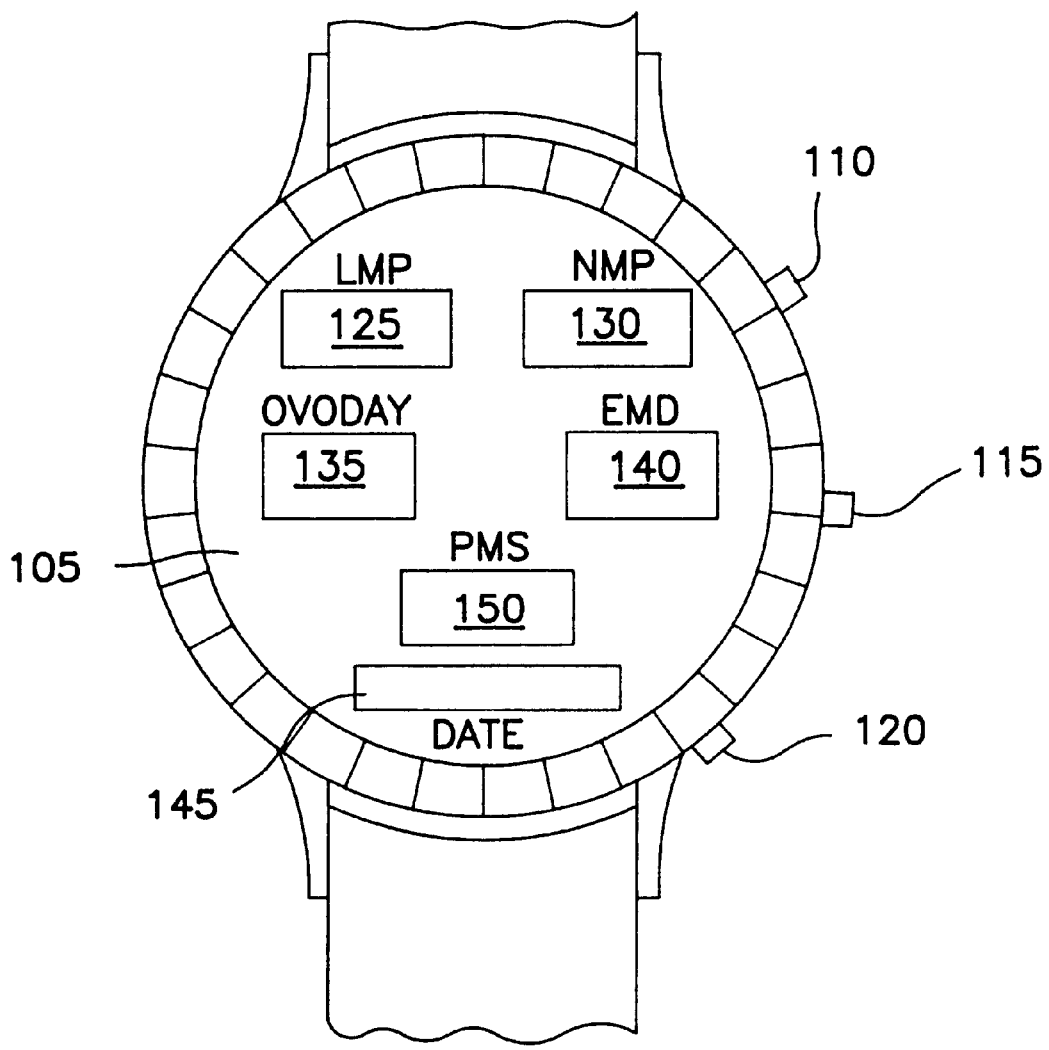
FIG. 2 is a plan view of an alternative embodiment of the present invention.

If desired, the day(s) a woman expects to experience PMS can also be displayed. Referring to FIG. 2, shown there is a display window 150 which indicates the day a woman expects to experience PMS. This day may be programmable from one to several days before the woman's next menstrual cycle. This feature is particularly important for those women who severely experience the associated symptoms of PMS.

Figure 3:
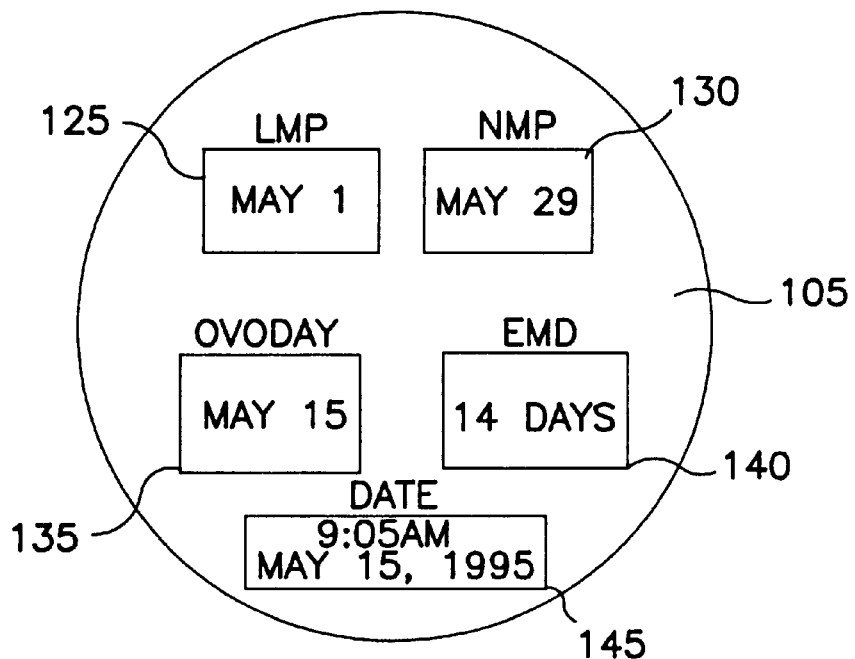
FIG. 3 is an illustrative view of the display of FIG. 1 as it would appear on May 1, 1995.
Figure 4:
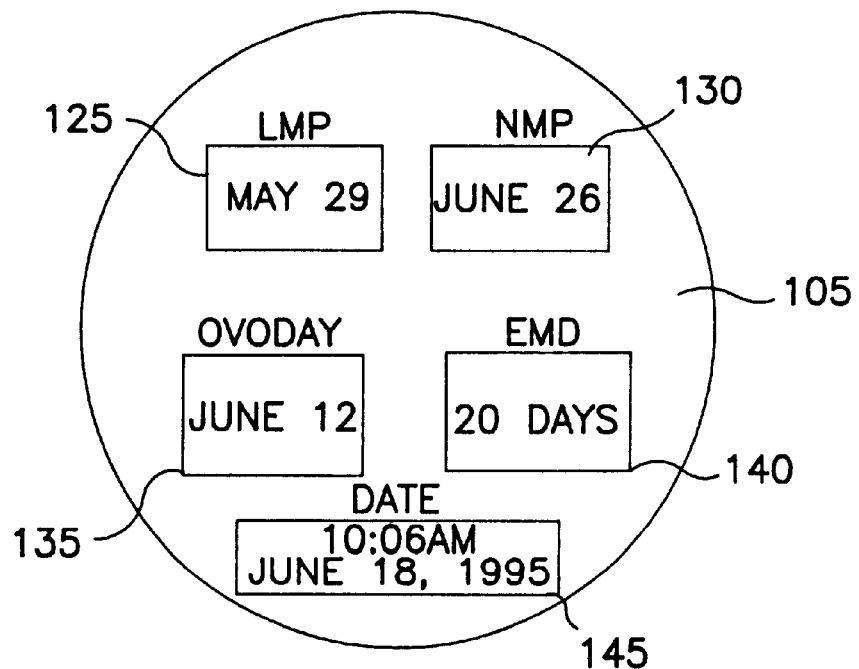
FIG. 4 is an illustrative view of the display of FIG. 1 as it would appear on Jun. 28, 1995.

FIGS. 3 and 4 show how the display windows would appear on May 15, 1995 and Jun. 18, 1995, respectively. As shown in FIG. 3, if a woman's last menstrual cycle was on May 1, 1995 display window 130 labeled "NMP" would display May 29, which is 28 days after the last menstrual cycle or period. It should be understood that on initial use, a woman must first enter the day of her menstrual cycle. In this case, the woman has entered "May 1".

Display window 140 labeled "EMD" would display "14 days" inasmuch as that many days have elapsed since the last men strual cycle or period. In addition, the current day (May 15, 1995) and time (9:05 a.m.) would be displayed in time/day display window 145. Also, display window 135 would display the ovulation day, in this case "May 15" which is 14 days prior to the next menstrual period.

Alternatively, the current day may be displayed in a standard calendar format with the days corresponding to "LMP," "NMP," and "ovoday" either boxed or highlighted.

The display windows are updated once a day at the end of each day. For example, on Jun. 18, 1995, several days after the next menstrual cycle had ended, the display windows would appear as shown in FIG. 4. The "LMP" display window 125 would now display "May 29" rather than "May 1". Likewise, the other display windows would have been updated, with "NMP" display window 130 now displaying "June 26" and "ovoday" display window 135 displaying "June 12". Since today would be Jun. 18, 1995, "EMD" display window 140 would display "20 days." This updating would be done automatically without the intervention of the user.

Inasmuch as menstrual wristwatch 100 cannot determine whether the woman's menstrual cycle occurred on time or on the "NMP" day, such information must be entered by the woman herself. Preferably, this can be done so by the woman simultaneously depressing pushbuttons 110 and 115 on the day menstruation starts. An audible tone may be used as a confirmatory signal that the date has been entered. In this manner, "LMP" display window 125 will subsequently display the actual day the woman had her last menstrual cycle. Likewise, simultaneously depressing pushbuttons 115 and 120 may be used to indicate the occurrence of ovulation.

In above instance, digital menstrual wristwatch 100 initially defaults to a 28-day menstrual cycle and an ovulation day occurring 14 days prior to the next menstrual period. Most women's menstrual cycles, however, deviate from those norms. Under such circumstances, when the digital wristwatch is first used, a woman will wish to directly adjust these default values to reflect her particular menstrual cycle. In that case, a woman will depress pushbutton 115 to place menstrual wristwatch 100 in a "setting" mode wherein the default value of the menstrual cycle (28 days) is displayed. By pressing either pushbutton 110 or pushbutton 120 a desired number of times, that default value can be either incremented or decremented, respectively. Once set, pushbutton 115 is depressed again and the default value for the ovulation day (14 days) is then displayed. Similarly, depressing pushbutton 110 or pushbutton 120 increments or decrements, respectively, the default value to suit the particular user. In this manner, the default values within the menstrual wristwatch can be set whenever a woman desires to do so. In a similar manner, a woman may press pushbutton 115 a third time to set the current day of the week, a fourth time to set the month, a fifth time to set the year and a sixth time to set the time (hour, minute, second).

As discussed above herein, a woman on the actual days of ovulation and menstruation confirms their occurrences by simultaneously depressing two pushbuttons. In response to the depression of the pushbuttons, the actual dates corresponding to the onset of menstruation or ovulation are stored in memory, such as in the form of a look-up table. In this manner, the digital menstrual wristwatch of the present invention accumulates the actual dates of menstruation and ovulation on a month-to-month basis. Importantly, the stored menstrual and ovulation dates provide a baseline from which to later change the menstrual data used to estimate the woman's next menstrual cycle or ovulation day. This latter menstrual data includes the number of days in the woman's menstrual cycle and the number of days prior to the next menstrual cycle during which ovulation occurs. That is, the woman's prior menstrual history may be used to account or monitor for variations in her menstrual cycle.

For example, at the end of the woman's next menstrual cycle, the device calculates for a predetermined number of previous months, the average number of days in the woman's previous menstrual cycles. This average is then may be used to estimate or calculate the date of the woman's next menstrual cycle.

Referring to the table below, if a woman's last menstrual cycle was on May 1, 1995 (Month No. 0), the "NMP" display window would initially display May 29. This is so because the wristwatch uses by default a 28-day cycle, unless changed by the woman. In the first month, however, the woman did not get her period until May 27, two days early of the calculated "NMP" day. At the end of the day on May 27, the display windows are updated. The "LMP" display window now indicates the actual day of the woman's last menstrual cycle, that is May 27. Inasmuch as the average number of days in the woman's menstrual cycle for the previous months is 27 days [(26 days+28 days)/2], the "NMP" window displays "June 27"which is 27 days after the last actual menstrual cycle.

In the following month, the woman's menstrual cycle likewise was not on time, beginning on June 25. That is, 29 rather than 27 days after the last actual menstrual cycle. For the then previous months, the average number of days in the menstrual cycles is now 27.6 days [(28 days+29 days+27 days)/3]. For the remaining four months, with the woman's menstrual beginning on July 23, August 17, September 7 and November 4, the corresponding number of days in the menstrual cycles are 29, 26, 24, 27 and 28 days, respectively. Accordingly, the average number of days in the woman's menstrual cycle for the then previous months are "27.25," "26.6," "26.6" and "26.8" days.

To estimate or calculate the day of the next menstrual cycle, the corresponding average number of days is added to the day of the woman's last menstrual cycle. In this case, those averages yield the following dates for the woman's next menstrual cycles: "August 17" (27.25 day cycle); "September 9" (26.6 day cycle); "October 6" (26.6 day cycle); and "November 4" (26.8 day cycle).

| Month No. | Days in Menstrual Cycle | Average Days in Menstrual Cycle For Previous Months | Next Menstrual Cycle | Last Menstrual Cycle |
| --- | --- | --- | --- | --- |
| 0 | 28 (Default) | 28 (Default) | May 29 | May 1 |
| 1 | 26 | 27 | June 23 | May 27 |
| 2 | 29 | 27.6 | July 23 | June 25 |
| 3 | 26 | 27.25 | Aug. 17 | July 21 |
| 4 | 24 | 26.6 | Sept. 9 | Aug. 14 |
| 5 | 27 | 26.6 | Oct. 6 | Sept. 10 |
| 6 | 28 | 26.8 | Nov. 4 | Oct. 8 |

Over time, irregularities in the woman's menstrual cycle will not abruptly, but gradually offset the number of days between the "LMP" and "NMP" so as more properly estimate when the woman can expect to get her period. Advantageously, a woman need not monitor how many days her cycle is off inasmuch as it is now performed automatically so long as she simply depresses the pushbuttons on the wristwatch to indicate the start of her menstrual cycle.

Alternatively, the device may calculate or estimate the woman's next menstrual cycle by always using a fixed number of days from the last menstrual cycle. This latter fixed number of days may be set by the woman. Or, the device may use simply the number of days in the woman's last menstrual cycle so as to more properly estimate the day of the woman's next menstrual period. Regardless of the method, it should be understood that each method only provides an estimate as to when a woman may expect to have her next menstrual cycle. None of the methods can actually predict when a woman will have her period inasmuch as there are too many unknown variables.

Similarly, the above methodologies may be used to estimate the woman's next ovulation day, which normally occurs 14 days before her next menstrual cycle. The ovulation day is displayed in display window 135. It should be understood that the onset of pre-menstrual syndrome may also be determined and displayed in a similar manner in display window 150.

Accordingly, the wristwatch of the present invention can be programmed to account or monitor for variations in a woman's menstrual cycle based on her past menstrual history. Various other programming techniques for effecting this latter methodology are well known in the art and may include the use of other statistical techniques, such as weight averaging, standard deviation and the like. It is also contemplated that artificial intelligence or logic called "fuzzy-logic" may also be used.

Figure 5:
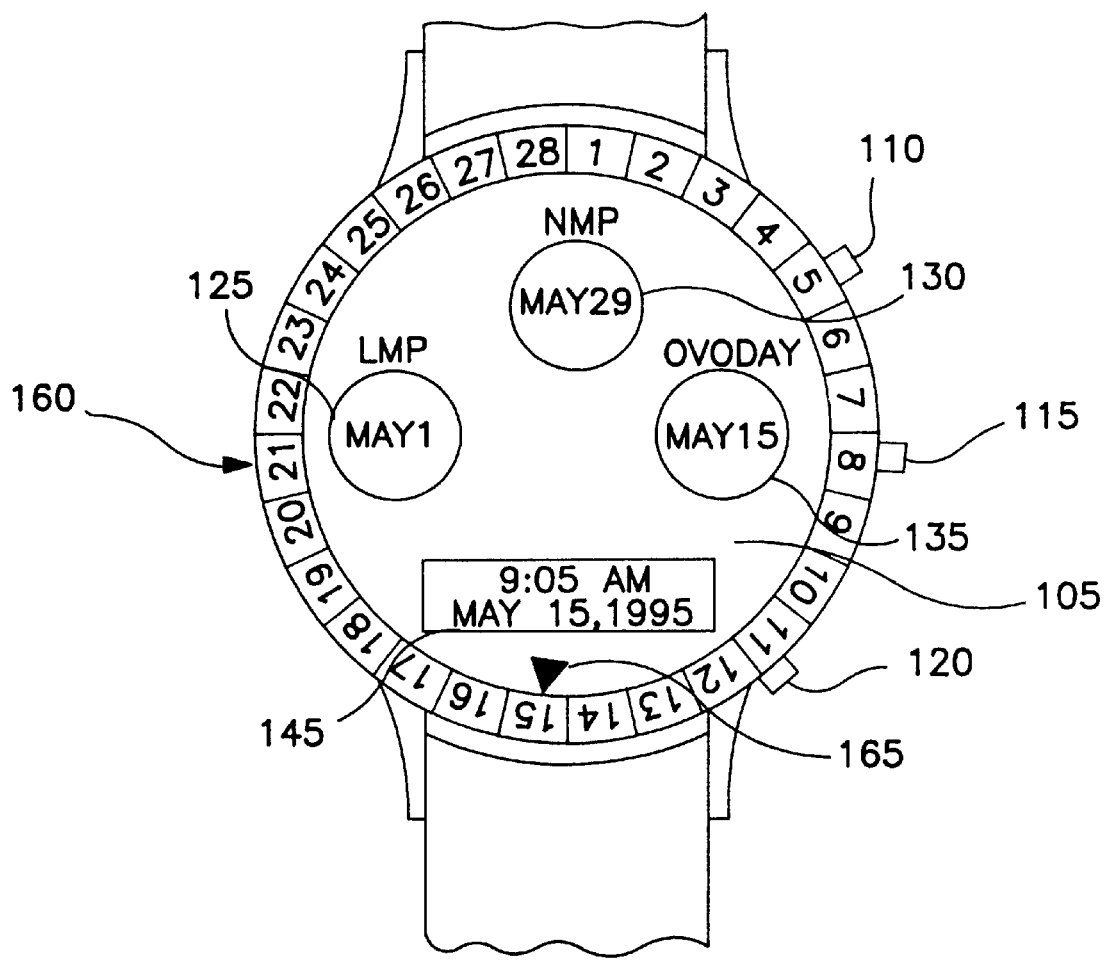
FIG. 5 is a plan view of another alternative embodiment of the present invention.

Referring now to FIG. 5, there is illustrated an alternative preferred embodiment of the present invention which is similar to the embodiment of FIG. 1, but differs from that embodiment in that an annular display portion 160 on the face of the watch is segmented into equally spaced numbered divisions. These divisions are used to visually indicate the number of days that have passed since the last menstrual cycle began, each division corresponding to an elapsed day. A display pointer 165 is positioned adjacent to the number of days since the woman's last menstrual cycle. It should be understood that other pointer or indicator means may be used. For example, the numbered divisions may be highlighted or blacken in the appropriate manner.

Although annular display 160 has only 28 days displayed, should the woman change the default setting, a corresponding number of divisions will then also be displayed. That is, if her menstrual cycle has 30 days, then 30 divisions would be displayed. Should the woman's menstrual cycle occur more than 28 days after her last cycle, the pointer simply wraps around, restarting on day number one. In this manner, a woman can readily observe how many days she is late.

An additional feature of the present invention is its programmable alarm capability. A woman may, if she desires, program the wristwatch of the present invention to alert her that she is within a given number of days ("target range") prior to menstruation. Similarly, other alarms may be programmed with respect to ovulation or pre-menstrual syndrome. Preferably, the alarm(s) are audible to the user, such as a sound, voice or word, either alarming on a single day or on a number of days prior to menstruation, ovulation and/or pre-menstrual syndrome. Of course, to indicate which alarm it is, a different sound or word may be used for each.

Figure 6:
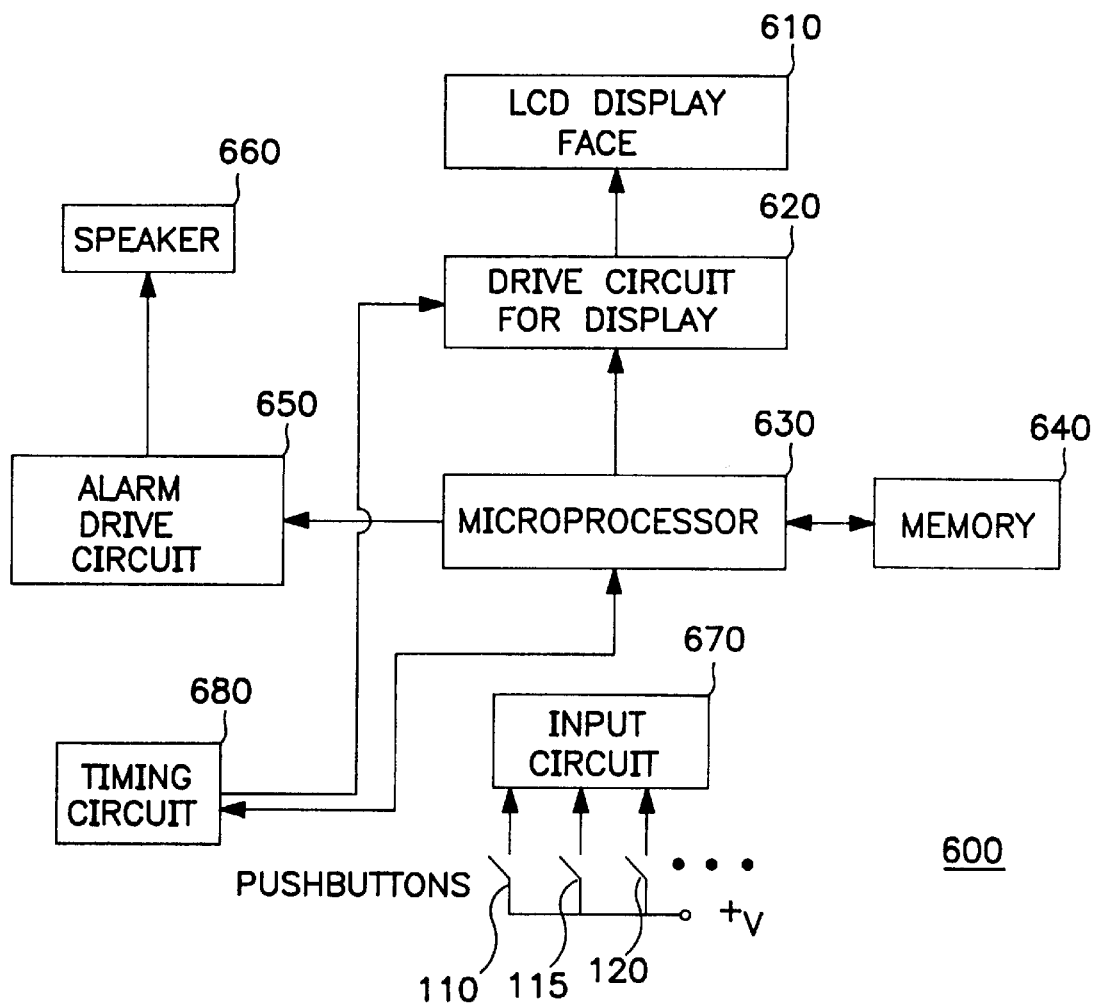
FIG. 6 is a functional block diagram illustrating the operation of the present invention.

FIG. 6 shows an illustrative functional block diagram of a control circuitry 600 of the invention. In this embodiment, control circuitry 600 includes eight distinct elements; LCD display face 610, display drive circuit 620, microprocessor 630, memory 640, alarm drive circuit 650, speaker 660, input circuit 670 and timing circuit 680. It should be understood, however, that the electrical circuits performing the functions of these elements need not be discrete and may be integrated in any manner, provided that the eight basic functions of these elements are performed.

The display function is performed by LCD display face 610 which operates in response to signals from drive circuit 620. LCD display face 610 comprises, for example, a dot matrix panel for at least displaying in predefined portions or windows thereof the date of the woman's last menstrual cycle, the date of the woman's next menstrual cycle, the number of days since the woman's last menstrual cycle and the current day and time. LCD display 610 may be in the shape of a circle, rectangle, or square.

More specifically, control circuitry 600 uses a microprocessor 630 having random access memory (RAM) 640 and internal hardware logic. Under program control, microprocessor 630 provides signals to drive circuit 620 so as to have displayed the menstrual data as discussed above in relation to FIGS. 3 through 4. That is, specific dots of the LCD display face are selectively activated by drive circuit 620 so as to display the appropriate data in display windows 125, 130, 135, 140, 145, 150 and 160. The display windows may be generated likewise in the shape of a circle, rectangle or square. Those skilled in the art will readily note that such menstrual data may alternatively be displayed, for example, using 7-segment LED displays.

It should be understood that microprocessor 630 includes such hardware as a central processing unit, program and random access memories, timing and control circuitry, input/output (I/O) interface devices and other digital subsystems necessary to the operation of the central processing unit. Also, those skilled in the art will readily note that the menstrual wristwatch of the present invention may be completely implemented using analog circuitry.

The digital wristwatch operates in accordance with a program whose methodology of operation is set forth above herein for displaying the above menstrual information or data. This program can be stored in conventional random-access-memory or in a preprogramed chip, such as EPROM or EEPROM. In particular, the program is made up of a number of instructions that are in coded binary format understood by the microprocessor, so that the program can tell the microprocessor how to calculate, for example, the date of the woman's next menstrual cycle, the number of days since the woman's last menstrual cycle, and the expected date of ovulation.

Control circuitry 600 is provided with timing circuit 680, preferably having a quartz crystal oscillator. Timing circuit 680 generates digital signals to drive circuit 620 corresponding to the current day, time, month and year. For example, timing circuit 680 may be a standard watch module. Timing circuit 680 updates the display, for example, once every hundredth of a second, so as to perform the clock function needed to keep track of time. These digital signals are also provided to microprocessor 630 so that it too knows the time and day. This time data is stored in RAM by the microprocessor and is updated on a need-to-basis.

The inputs to the microprocessor are entered through input circuit 670 and pushbutton 110, 115, 120. Input circuit 670 may use standard buffers and encoders, which are well known in the art. Preferably, whenever any of the pushbuttons are depressed, an interrupt signal goes to microprocessor 630, causing it to execute the appropriate interrupt routine necessary to read the inputs from the pushbuttons.

The function of alarm drive circuit 650 is, in response to digital signals from microprocessor 630, to generate audible tones at different frequencies via a speaker 660. These tones indicate different times within a woman's menstrual cycle in relationship to a woman's menstruation, ovulation or PMS. The operations of such alarm drive circuits are well known in the art and accordingly will not be discussed here for the sake of clarity.

Figure 7:
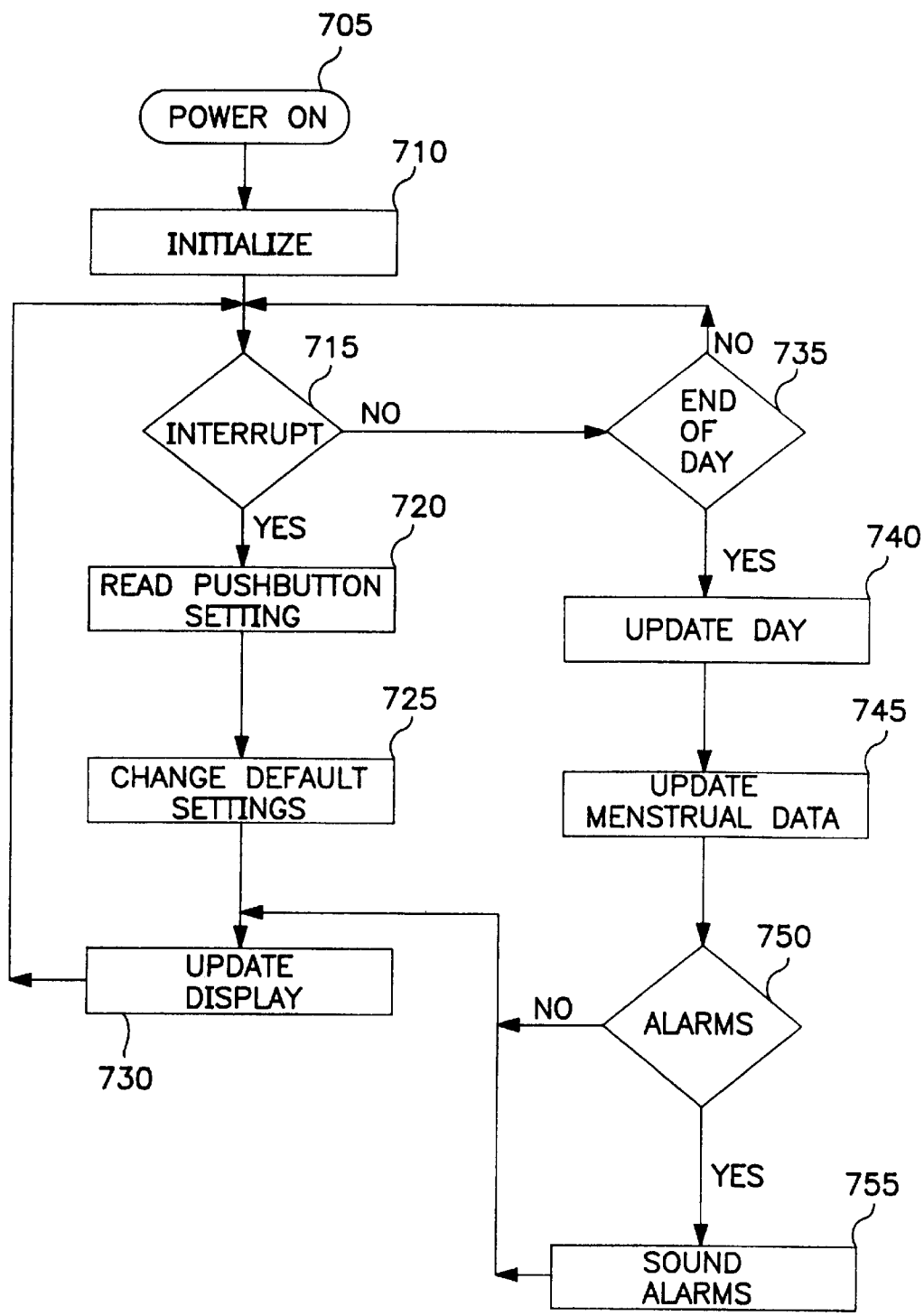
FIG. 7 is a flow chart of an illustrative program for the microprocessor of FIG. 6.

The operation of microprocessor 630 of FIG. 6 can be understood more clearly from the flow chart of FIG. 7, together with the following discussion. As shown in FIG. 7, the operation of the microprocessor 630 is centered, in part, around the detection of an interrupt in decision block 715. It is necessary, however, that a portion of the control program stored in memory provides a routine for initializing microprocessor 630 when power is first applied. Therefore block 705 indicates a power on condition, and block 710 indicates that the microprocessor is initialized. In block 710, a routine is executed which initializes a number of registers in memory. Some of these registers correspond, for example, to the default settings for the number of days in a woman menstrual cycle, the number of days prior to the next menstrual that ovulation occurs and a default setting for the woman's last menstrual cycle (day, time, month and year). Other registers will also be initialized relating to alarm settings discussed above herein. Once the initializing has been completed, it need not be repeated until the microprocessor is turned off and then turned on again, such as when there is a loss of power due to battery failure. To alleviate this problem, however, it is contemplated that the menstrual wristwatch of the present invention includes a backup battery.

Decision block 715 tests the interrupt line setting to the microprocessor to determine whether any of the pushbuttons have been depressed and hence have send out an interrupt request. Should the pushbuttons be repeatably depressed, an appropriate interrupt may be generated to indicate so. If so, the microprocessor reads the pushbutton settings, and accordingly changes the default settings, as discussed above and shown in blocks 720 and 725. For example, the number of days in the woman's menstrual cycle may have been changed or the date of the woman's last menstrual cycle set for the first time. If the user, however, sets the current time, day, month and year, the microprocessor will accordingly instruct the timing circuit to do likewise.

After testing for an interrupt signal, the microprocessor will check in block 730 to see if it is the end of the day. If so, the microprocessor updates in block 735 its internal registers that keep track of the current day. When this has been completed, the microprocessor updates the woman's menstrual data, as shown in block 740. Unless the woman has indicated that menstruation has started, the number of days displayed since her last menstrual cycle is incremented by one. If the woman, however, has indicated so, the "LMP" display window is replaced with the actual date of her menstruation. Moreover, the microprocessor, using, for example, the average number of days in her menstrual cycles for the prior months, determines the date of her next menstrual cycle as discussed above herein. Similarly, information relating to the woman's ovulation and, if displayed, information relating to her PMS is updated.

At the end or the start of each day, the microprocessor checks in block 750 for alarm settings. If the current day is equal to or within a programmable number of days to any of the alarm setting set by the woman, the microprocessor causes an audible tone to be heard by the woman at a predetermined time of day.

When these routines are completed, the microprocessor proceeds to update the information on the LCD display face. This step consists of sending the appropriate data to the drive circuit so as to permit the drive circuit to display the correct menstrual data. Afterward the microprocessor loops back to the beginning so as to start the entire process over again.

Over several months, the menstrual wristwatch accumulates menstrual data which is stored in memory. It is contemplated that the digital menstrual wristwatch of the present invention may be interfaced with an external computer like the IBM PC or the Apple Macintosh thru a external port. In this manner, a woman's menstrual data may be downloaded for medical diagnostic purposes, among other things. The wristwatch can also interface with small hand-held pocket computers like those readily available from Texas Instrument, Hewlett Packard, and Casio, among others.

It should be emphasized that the above described flow chart, shown in FIG. 7, is merely one example of how microprocessor 630 may be programmed in order to control LCD display face 610. Similarly, the combination of components shown in FIG. 6 could be changed to meet specific design requirements, such as requirements for additional inputs or different types of displays or timing circuits.

Thus, it is understood that the embodiment herein is merely illustrative of the principles of the invention. Various modifications may be made by those skilled in the art which will embody the principles of the invention and fall within the spirit and the scope thereof.

What is claimed is:

1. A device for monitoring the menstrual cycle of a woman, said device comprising:

a housing;

memory means for storing associated dates of the woman's menstrual cycle;

a display disposed on said housing;

display drive means responsive to said memory means for displaying said associated dates of the woman's menstrual cycle on said display;

without user intervention, means for automatically updating from day to day said associated dates of the woman's menstrual cycle on the basis of both said menstrual data stored in said memory means and the current date; and means for adjusting said menstrual data so as to reflect the woman's particular menstrual cycle.

2. The device of claim 1 wherein said means for adjusting includes pushbutton means for changing the associated dates of the woman's menstrual cycle stored in said memory means.

3. The device of claim 1 wherein said means for adjusting includes means for entering into said memory means the date when the woman's menstrual cycle begins.

4. The device of claim 1 wherein said dates associated with a woman's menstrual cycle include the date of the woman's last menstrual period, and the date of the woman's next menstrual period, and said menstrual data includes the number of days in the woman's menstrual cycle.

5. The device of claim 1 wherein said dates associated with a woman's menstrual cycle further includes the date of a woman's ovulation, and the date a woman expects to experience pre-menstrual syndrome.

6. The device of claim 1 further comprising timing means for generating signals corresponding to the current time and day, and said display drive means further for displaying said current time and day on said display.

7. The device of claim 6 further comprising means for setting the timing means to the current time and day.

8. The device of claim 1 wherein said means for updating includes means for estimating the date of the woman's next menstrual cycle.

9. The device of claim 8 wherein the date of the woman's next menstrual cycle is a predetermined number of days from the date of the woman's last menstrual cycle.

10. The device of claim 9 wherein said predetermined number is a statistical number of days from the date of the woman's last menstrual cycle, said statistical number of days based on the woman's prior menstrual history.

11. The device of claim 1 wherein said display includes a plurality of predefined display windows, said dates associated with a woman's menstrual cycle being displayed within said display windows.

12. The device of claim 1 wherein said display includes an annular display portion segmented into numbered divisions, each corresponding to an elapsed day, said device further comprising pointer means for indicating on said annular display the number of days that have elapsed since the date of the woman's last menstrual cycle.

13. The device of claim 1 further comprising means for alerting the woman at predetermined times within her menstrual cycle.

14. The device of claim 1 wherein said display drive means further displays said dates associates with a woman's menstrual cycle in conjunction with a standard calendar display.

15. The device of claim 1 wherein said display drive means further displays the number of days since the date of the woman's last menstrual cycle.

16. A menstrual monitor comprising a housing;

a display face on said housing having a plurality of predefined display windows;

means for displaying the dates of a woman's last and next menstrual cycles, each of said dates being displayed in one of said plurality of predefined display windows;

means for storing menstrual data;

means for calculating the date of the woman's next menstrual cycle on the basis of said menstrual data, the current date and the date of the woman's last menstrual cycle;

means for accessing said menstrual data; and without user intervention, means for automatically updating from day to day the date of the woman's next menstrual cycle on the basis of said menstrual data and the current date.

17. The menstrual monitor of claim 16 further comprising pushbutton means for changing the date of the woman's last menstrual cycle.

18. The menstrual monitor of claim 16 further comprising means for setting the date when the woman's menstrual cycle begins.

19. The menstrual monitor of claim 16 wherein said means for displaying further displays the date of the woman's ovulation, and the date a woman expects to experience pre-menstrual syndrome.

20. The menstrual monitor of claim 16 further comprising timing means for generating signals corresponding to the current time and day, and said means for displaying further displaying said current time and day on said display face.

\* \* \* \* \*